United States Patent
Dewan

(10) Patent No.: US 6,497,718 B1
(45) Date of Patent: Dec. 24, 2002

(54) PROCESS FOR PHASE-LOCKING HUMAN OVULATION/MENSTRUAL CYCLES

(75) Inventor: Edmond M. Dewan, Lexington, MA (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 23 days.

(21) Appl. No.: 09/851,223

(22) Filed: May 9, 2001

(51) Int. Cl.[7] .................................................. A61N 5/06
(52) U.S. Cl. ........................................................ 607/88
(58) Field of Search .............................. 607/88, 90, 91; 351/47, 44; 606/1

(56) References Cited

U.S. PATENT DOCUMENTS 5,274,403 A * 12/1993 Gott ............................ 351/165

OTHER PUBLICATIONS

Lin, M.C. et al., Psychiatry Research, 1990, V33, N2, p. 135–138.*
Criss, T.B. et al., Social Biology, 1981/1–2, p. 75–80.*

* cited by examiner

Primary Examiner—Roy D. Gibson
(74) Attorney, Agent, or Firm—William G. Auton

(57) ABSTRACT

A luminescent ovulation/menstrual cycle adjustment process to entrain preselected biorhythms with a scheduled regimen of photic stimulation. This process is performed by subjecting a woman subject to a nocturnal light exposure that corresponds exactly to a lunar cycle of 29.5-days.

3 Claims, 3 Drawing Sheets

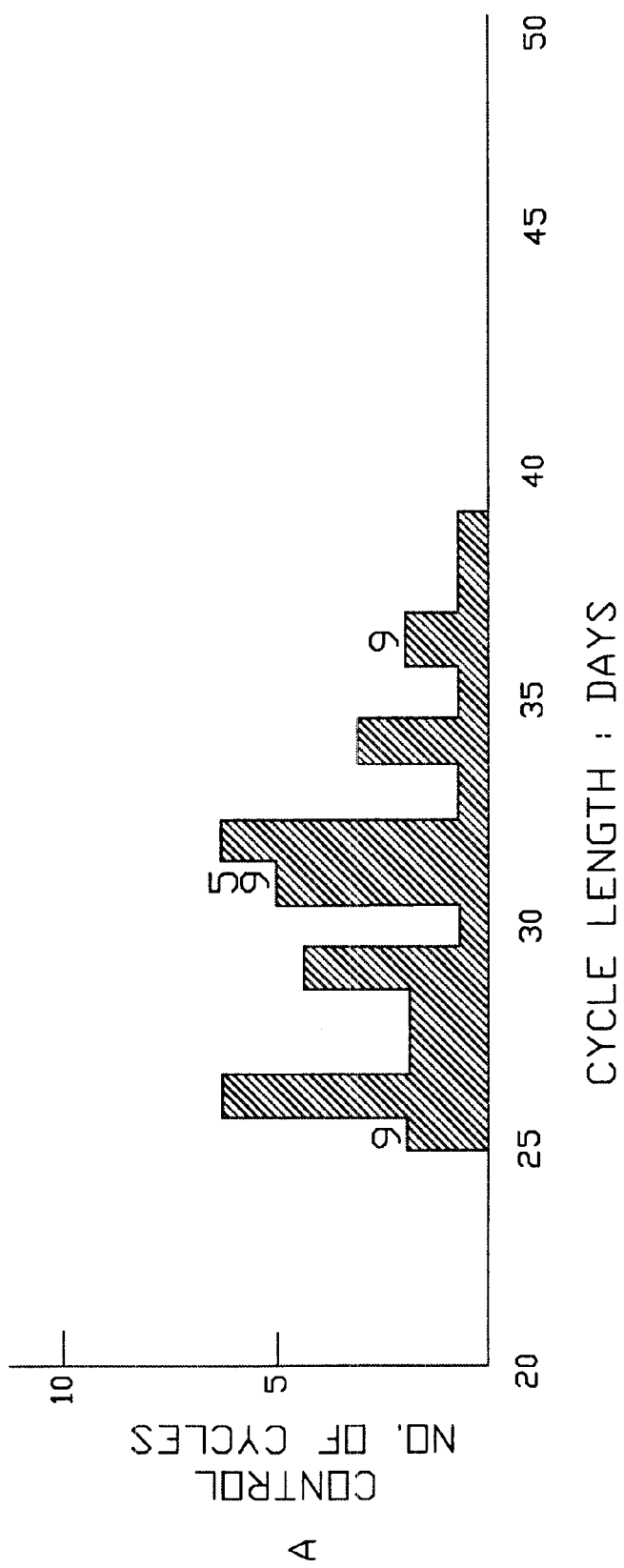
FIG. 1-A

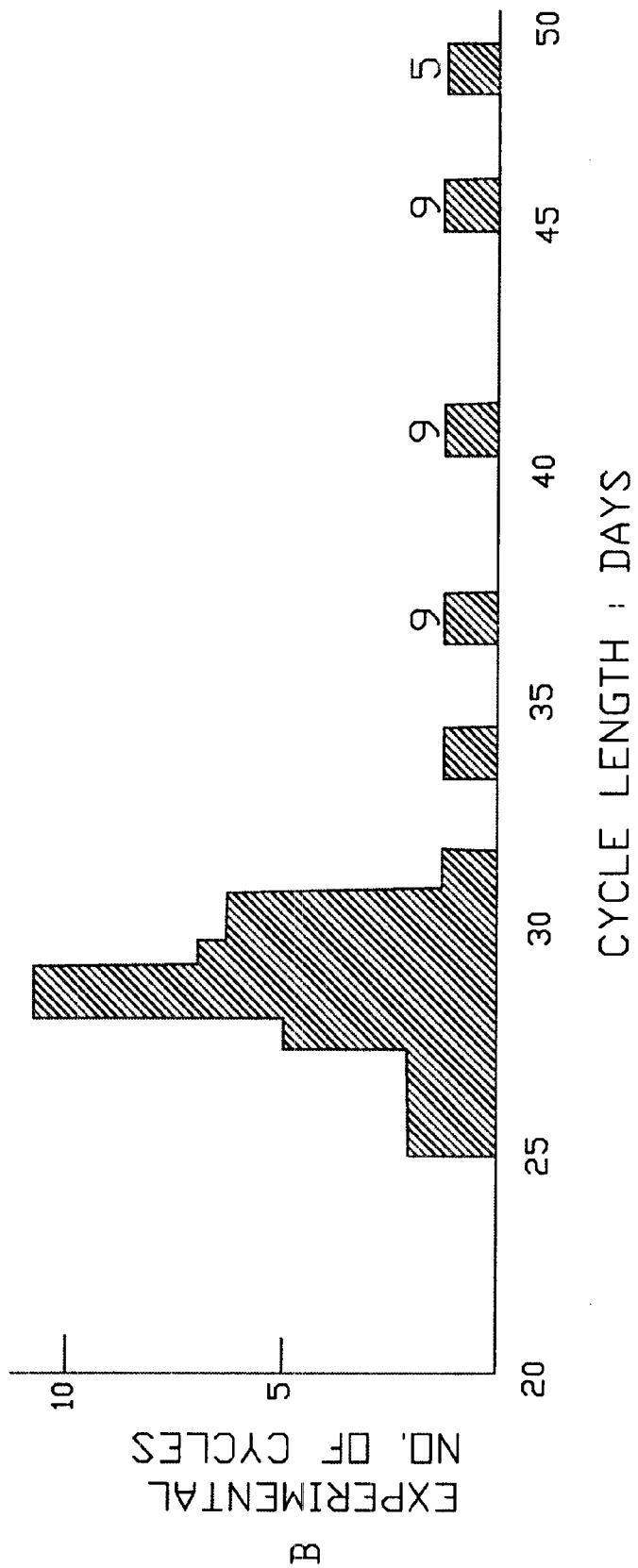
FIG. 1-B

PROCESS FOR PHASE-LOCKING HUMAN OVULATION/MENSTRUAL CYCLES

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to luminescent biorhythm cycle adjustment systems and more specifically to a process for phase-locking human fertility or menstrual cycles. Luminescent biorhythm adjustment on some mammals has been implemented in such milestones as U.S. Pat. No. 6,210,923, Apr. 3, 2001, Mammalian circadian regulator M-RIGUI2 (MPER2), Lee, Cheng-chi, U.S. Pat. No. 5,562, 719, Oct. 8, 1996, Light therapy method and apparatus, Lopez-Claros, and U.S. Pat. No. 5,923,398, Jul. 13, 1999, Interactive light filed for non-visual stimulation, by Goldman, the disclosures of which are incorporated herein by reference.

If the period of the fertility cycle of a woman could be influenced in some way to become highly regular, then the rhythm method, which has serious drawbacks at present, would become a valuable and reliable technique for birth control. It would be especially valuable for populations that are culturally, economically, or medically prevented from using other methods currently available.

It is very common in biology to find synchronization or "entrainment" phenomena between environmental influences and various types of rhythms, such as EEG, ECG, and circadian rhythms. This "entrainment" or "locking in step" phenomenon can also result in a regularization effect. This is illustrated in FIG. 2, which shows the regularization of an irregular electronic oscillator, by entrainment with a very regular external periodic stimulation. Therefore, it seems useful to consider the possibility of entraining the ovulation cycle. While there are encouraging indications that this might be accomplished by the periodic administration of drugs, one should not overlook the possibility of photic stimulation, since it is well known that photic stimulation can profoundly affect the pituitary-gonadal function in many vertebrates.

Estrus and ovulation regulation is more often accomplished by hormonal and chemical agents as shown in such references as U.S. Pat. No. 5,721,278, Feb. 24, 1998, Ovulation control by regulating nitric oxide levels, Garfield, Robert E., and U.S. Pat. No. 5,589,457, Dec. 31, 1996, Process for the synchronization of ovulation, by Wiltbank.

During research, Edmond Dewan reported that by simulating moonlight with nocturnal light exposures, the menstrual cycles of women could be brought nearer to the lunar cycle of 29.5 days. Dewan argued that such dim light might be used to augment natural contraceptive methods. More specifically, claims that a bedside 100-watt bulb could stabilize irregular menstrual cycles, was initially greeted with skepticism. Recent studies of light treatments of humans have indicated that both bright and dim light have real biological effects. To examine the validity of these ideas, experiments have treated two samples of women with irregular menstruation with randomly assigned 100-watt bedside night lights or dim red light placebos. In both groups, the 100-watt treatments significantly decreased the duration of menstrual cycles and reduced their variability.

A need exists for a practical process to implement the use of light to regulate menstrual cyclicity. The present invention is intended to satisfy that need.

The phenomenon of "entrainment" or "phase-locking" of circadian cycles in animals, including humans, by means of light-dark cycles of approximately 24 hour periods is now well known. It is also known that these cycles in man are of importance to the military (e.g. jet lag, nocturnal operations, etc.) The question raised here is whether or not another human biological oscillation, namely the fertility cycle of about 28 days, is also of interest to the Air Force.

In the sixties a paper was published entitled "On the possibility of a perfect rhythm method of birth control by periodic light stimulation" in the American Journal of Obstetrics and Gynecology, 99, 1016–1019 Dec. 1, 1967. In this paper, some preliminary evidence was shown that suggested that the menstrual cycles of women could be regularized by means of light. Later on, further evidence for this effect on a larger population was published by Dewan et al. in "Effect of photic stimulation on the human menstrual cycle" Photochemistry and Photobiology, 27, pp. 581–585 (1978). Still more recently a paper by Daniel F. Kripke entitled "Light regulation of the menstrual cycle" was published in a book edited by L. Wetterberg "Light and biological rhythms in man" Pergamon Press 1993, ISBN 0-08-0422799. Dr. Kripke repeated the earlier experiments mentioned above and found independent evidence for the regularization effect of the light schedule on the human fertility cycle. The mechanism for this effect may involve the pineal gland, the superchiasmic nuclei, the hypothalamus, melotonin and HIOMT. The original aim of the research was to see if light could serve as a "zeitgaber" or synchronizer of these cycles. One practical application would be a method to make the so-called "rhythm method of birth control" much more accurate. This could be used either to enhance or to avoid conception. From a purely scientific standpoint, the possibility of phase-locking human fertility cycles by means of periodic photic stimulation would have far reaching implications in biology of a fundamental nature.

An important question is whether or not such a possibility would be of practical value to the Air force. For example, would it be useful or beneficial in any way for women in the military to have highly predictable fertility cycles? The second question is whether or not the scientific issue involved should be explored as a basic question of general importance to our understanding, so that future practical problems, not now envisioned, can be solved.

The practical outcome of research on this subject could be a device that would control the brightness and schedule of light in a bedroom (or device covering the eyes) during sleep that would phase-lock human ovulation cycles. The idea behind it is that, during evolution, the fertility cycle of humans and other primates was phase-locked to the moon and that full moon coincided with ovulation. In other words, the original zeitgaber of the human 28-day cycle was the 28-day lunar cycle. Recently published papers show that this idea is no longer as strange as it appeared in 1967 when it was first proposed. The reason for this is that one now knows (as was not known then) that (a) light has such a large hormonal effects that it can be used to cure seasonal affective disorder, (b) the circadian cycles in humans can be phase-locked to light schedules. (Kronauer and Czeisler at Harvard showed this, see page 217 of Wetterberg's book cited above), and (c) the roles of various organs of the brain, nervous system, and the underlying biochemistry have become better understood the last 33 years.

SUMMARY OF THE INVENTION

The present invention is a luminescent ovulation/menstrual cycle adjustment process to entrain preselected biorhythms with a scheduled regimen of photic stimulation. The process is implemented by a control of the brightness and schedule of light in a bedroom (or device covering the eyes) during sleep that would phase-lock human ovulation cycles. The idea behind it is that, during evolution, the fertility cycle of humans and other primates was phase locked to the moon and that full moon coincided with ovulation. In other words, the original zeitgaber of the human 28-day cycle was the 28-day lunar cycle. The attached discussion shows that this idea is no longer as strange as it appeared when is was first proposed. The reason for this is that one now knows (as was not known then) that (a) light has such large hormonal effects that it can be used to cure seasonal affective disorder, (b) the circadian cycles in humans can be phase-locked to light schedules.

In one embodiment of the invention, the process is accomplished by subjecting a woman subject to a nocturnal light exposure that corresponds exactly to a lunar cycle of 29.5-days, said nocturnal light having a schedule of brightness and darkness with a maximum nocturnal brightness corresponding to a full moon, and diminishing to zero brightness corresponding to the new moon; and repeating with regular periodicity. The schedule need not be in phase with the actual moon of course but could be chosen for convenience.

DESCRIPTION OF THE DRAWINGS

FIGS. 1 (A and B) show respectively a histogram of 41 control menstrual cycle lengths (A) and of 41 matched experimental cycle lengths (B) in 16 women: Day 14 through 17 light regimen. The eight cycles from subjects No. 5 and No. 9 are explicitly labeled.

DETAILED DESCRIPTION OF THE PREFERRED EMBODIMENT

Figure 2:
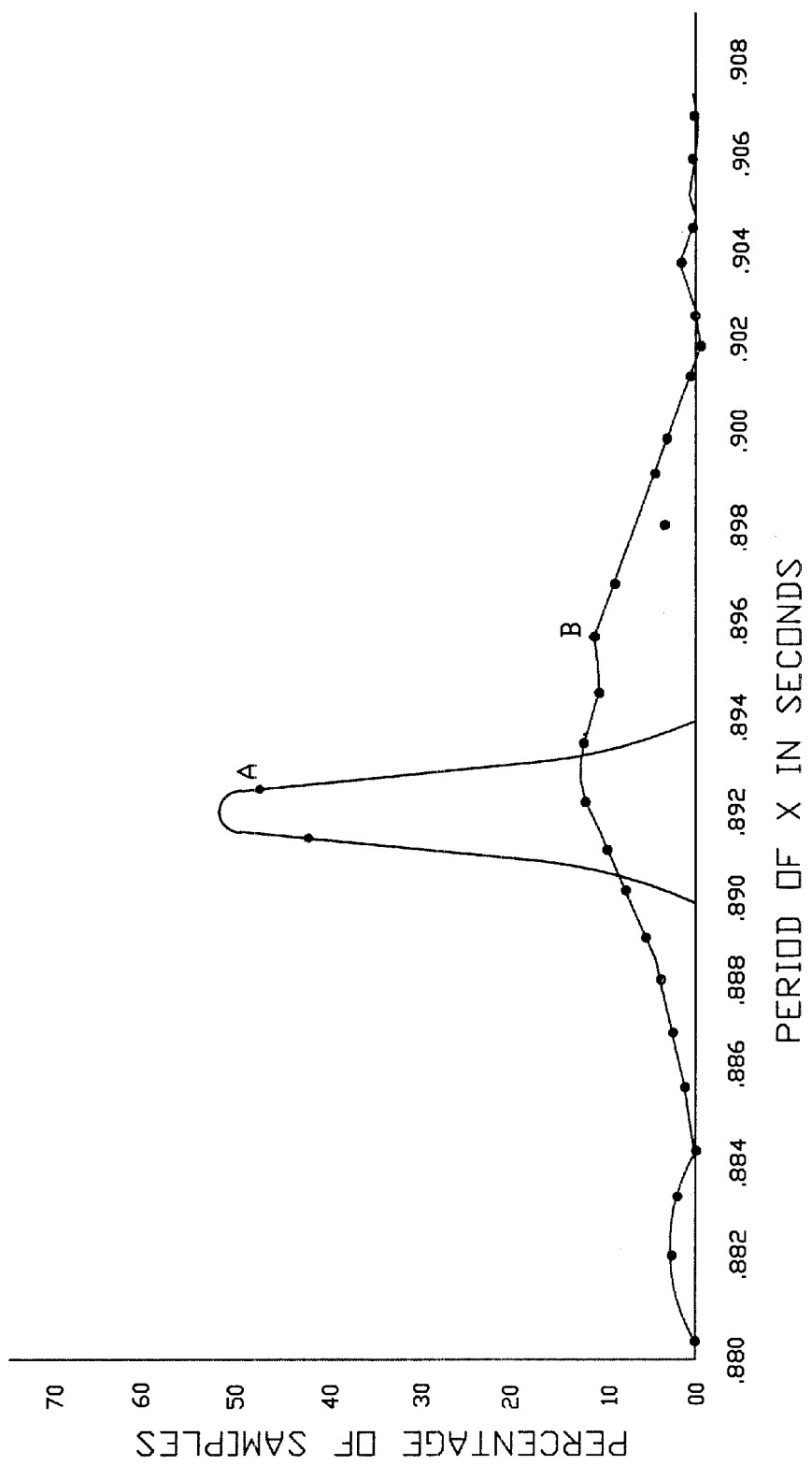
FIG. 2 depicts histograms of 200 periods of an electronic oscillator with irregular frequency. A shows the irregularity of the periods. B shows the regularity induced when the oscillator is entrained to an external regular oscillation.

The present invention is a luminescent ovulation/menstrual cycle adjustment process to entrain preselected biorhythms with a scheduled regimen of photic stimulation. The field of biology is well known for it's many rhythms or "biological clocks". The so-called "circadian rhythm" has received the most attention. One of the striking features of circadian oscillations is their property of becoming synchronized or "phase-locked" to the 24-h light and dark schedule of environmental illumination. In a similar manner, biological rhythms of cycle-length approximating the lunar period have also been shown to exhibit this synchronization property with respect to environmental lighting conditions. Apparently the sexual cycles of marine animals as well as certain terrestrial mammals can be phase-locked to the full moon in this manner.

The menstrual cycle in humans and some other primates has long been associated with the moon. The very word menstruation, the onset of which initiates the female cycle has, as its derivation connotes, long been related to the moon. Although, for many years, the so-called "normal" human menstrual cycle was regarded as 28 days long, statistical evidence support the view that a 29-day cycle should be considered as the norm. Substantiation of this concept is afforded by the voluminous study of Treloar et al (1967) who complied well over 270,000 cycle lengths of women throughout all ages of reproductive life. Although these data are most striking for the large amount of variability which they display, the mean values of these cycles are in the vicinity of 29 days. The mean synodic lunar month is 29.53 days; and the theory behind the present invention suggests that this similarity may not be mere coincidence. The speculation is that, during evolution, there may have been a selective advantage for those who ovulated in synchrony with a particular phase of the moon. If this were correct, then two predictions can be made: namely, primates living at the equator ovulate in synchrony with a certain phase of the moon, and similarly, women living at the equator, under very primitive conditions out in the open, would also have cycles synchronous with the moon phases. The equator would be the ideal location for this phenomenon due to the regularity of the environmental lighting conditions there as well as the mild weather which permits a minimum of protection from the environment and hence more opportunity to be exposed to natural light, especially nocturnal moonlight.

With regard to the first prediction above, an encouraging observation was reported by Hille (1842) of a monkey that menstruated at every new moon in Surinam, South America (essentially at the equator). Ovulation apparently took place at full moon. The hypothesis that ovulation occurred in the human at full moon during evolutionary times has an interesting implication. Natural selection would favor the tendency to mate at this time of month (say for example due to the ability to see at night) would favor, again by natural selection, the tendency to ovulate at the time of full moon. If this speculation were correct, it would provide not only an evolutionary explanation of the phenomenon here studied. It would also explain, on a rational basis, the cause of the well-known "romantic" effect of the full moon.

In connection with the second prediction, there unfortunately has as yet been no study to determine if the fertility of women living at the equator under primitive conditions is related to the full moon. However, Hoseman (1950) has demonstrated a common folklore belief that the onset of menses in native women in the tropics is synchronized to the new moon. In addition it has been noted that the sexual cycles of certain prosimians are characterized by an active phase synchronized to the full moon.

Sunlight also is instrumental in inducing ovulation as is evidenced by a striking seasonal increase in the number of multiple pregnancies occurring in Finland during the spring and summer months when there are more sunlight hours than in the dark winter months.

The question arises as to what physical influence could be the synchronizing agent in these cycles. In the case of the circadian rhythms, the primary synchronizing cue is, as has already been mentioned, the schedule of light and darkness. This is also true in the one case of lunar periodicity that has been tested in the laboratory by Hauenschild. Hence the possibility exists that the same could be true for human ovulation. This can be tested by the use of a schedule of artificial light in a manner to be described below.

That artificial light can increase egg production in chickens is well known, and it is also recognized that artificial light schedules can affect the sexual cycles of mammals.

The mechanism for such an effect has been delineated by Wurtman (1969) who reported that, whereas melatonin, a hormone produced in the pineal gland, inhibits ovarian function, the synthesis of this hormone is, in turn, inhibited by light.

Collu et al (1971), as well as Ying and Greep (1973) have demonstrated the suppressive effect of melatonin on ovulation in rats while Fiske and MacDonald (1973) have reported similar findings in monkeys. Impairment in the release of LH secretion may be involved here. It is indeed significant that the mechanism for ovulation synchronization by means of light has thus been already shown to exist in primates.

Over 30 years ago Dewan suggested that the synchronization of the ovulation cycle in women by an artificial environmental light schedule might afford a simple and drugless means of regularizing the length of the human menstrual cycle to a degree which would facilitate the use of the rhythm method of birth control. As now practiced, either alone or in conjunction with basal body temperature, it is unreliable, as several studies have shown, and as Ogino (1962) himself has admitted. Furthermore, according to Mikamo and Iffy (1974), midcycle abstinence increase the danger of pregnancy complications and birth defects due to the fertilization of overripe as well as immature ova.

If the time of ovulation could be pinpointed, this method, used alone or in conjunction with other methods, could be highly practical. It could also be used to enhance the probability of pregnancy if that were the objective.

To test his hypothesis that artificial light can be used to regularize the human menstrual cycle, Dewan (1967) performed a pilot experiment on a 26-year old woman whose previous cycles had varied between 33 and 48 days. Exposure to all-night light while asleep during the nights of cycle days 14 through 16 or 17 (day 1 being defined as the first day of menstrual flow) had the effect of causing her cycle to become more regular. The five experimental cycles ranged in length from 29 to 31 days.

With the encouraging results of this test case it seemed worth while to continue the experiment on a larger scale. The subjects studied were 15 female patients of the Rock Reproductive Clinic, Inc. In addition the original data of the previously mentioned subject was included and hence there was a total of 16 subjects who reported a history of menstrual irregularity and/or abnormally long cycles. With one exception, the range in age was 21 to 36 years.

The rationale for our procedure was based on the adoption of a 29-day cycle as the "normal" length. In such a cycle, with menstruation occurring on day 30, ovulation should theoretically occur on day 15. For this reason, light exposure was started on the evening of day 14 with the hope that ovulation would be triggered by day 15, hence menstruation on day 30, i.e. a 29-day cycle. The light regimen was continued for two, or preferably, three nights more. This procedure can be regarded as an artificial simulation of the effects of full moon, which illuminates several consecutive nights. Future experiments could test for the possibility of synchronization by locking the light schedule to the calendar rather than to the woman's cycle.

The detailed procedure for the experiment was as follows. A common table lamp fitted with a 100 W incandescent bulb and with a shade open at the top was placed on the floor about 10 ft from the head of the bed. The illumination reflected from a diffuse area on the ceiling made it less disturbing during sleep.

The subjects were instructed to leave the light on all night during sleep for the entire nights of cycle-days 14 through 17, the first day of flow being designated as day 1 (thus day 14 is 2 weeks minus 1 day from the start of menses). On all the other nights of the cycle the women were told to make sure that light was completely avoided after retiring. They were instructed not to wear eyeshades during the nights that the light was on and to avoid anything that would artificially block the light in any other way (for example, by putting their heads under blankets or pillows) since the hypothesized effect of the light would be through a pathway from the eyes to the pineal gland. Temperature charts were furnished on which the patients were asked to record their basal body temperature, as well as the dates of menses and of exposure to light.

According to the temperature graphs, all of the subjects in this study were ovulating. One subject (No. 15 and not included here) consistently had flat temperature graphs. In addition, one of her cycles had a length of 108 days. It was presumed, for no reasons, that she was not ovulating.

TABLE 1

Photic Stimulation of Menstrual Cycle
Effect of mid-cycle photic stimulation on 41 menstrual cycle lengths of 16 women aged 16 to 36 years. "A" signifies that the cycle occurred after the regimen with light. The experiment, in each case, lasted for months, not years.
Menstrual cycle length (days)

| Age | Subject | Control (A) | Experimental (B) | Subject | Control (A) | Experimental (B) | Age |
|---|---|---|---|---|---|---|---|
| 26 | 1 | 28 | 29 | 9 | 31A | 41 | 21 |
|  |  | 32 | 31 |  | 36A | 37 |  |
|  |  | 26 | 28 |  | 25A | 46 |  |
|  |  | 37 | 27 | 10 | 29A | 31 | 16 |
| 28 | 2 | 36 | 28 | 16 | 28 | 28 | 33 |
|  |  | 32 | 28 |  | 35 | 30 |  |
|  |  | 34 | 29 | 17 | 26 | 29 | 36 |
|  |  | 34 | 30 |  | 29 | 30 |  |
|  |  | 34A | 30 | 18 | 29 | 29 | 25 |
| 30 | 3 | 26 | 28 |  | 27 | 26 |  |
|  |  | 32 | 29 | 21 | 25 | 25 | 31 |
|  |  | 29 | 31 | 22 | 31 | 31 | 35 |
|  |  | 30 | 31 |  | 33 | 32 |  |
| 32 | 5 | 31 | 49 | 23 | 26 | 30 | 36 |
| 27 | 6 | 32 | 29 |  | 31 | 30 |  |
|  |  | 32 | 29 | X | 32A | 29 | 26 |

TABLE 1-continued

Photic Stimulation of Menstrual Cycle
Effect of mid-cycle photic stimulation on 41 menstrual cycle lengths of 16 women aged 16 to 36 years. "A" signifies that the cycle occurred after the regimen with light. The experiment, in each case, lasted for months, not years.

Menstrual cycle length (days)

| Age | Subject | Control (A) | Experimental (B) | Subject | Control (A) | Experimental (B) | Age |
|---|---|---|---|---|---|---|---|
| 27 | 7 | 26 | 29 |  | 32A | 29 |  |
|  |  | 26 | 25 |  | 29A | 31 |  |
|  |  | 27 | 27 |  | 38A | 30 |  |
|  |  | 26A | 26 |  | 31A | 29 |  |
| 34 | 8 | 31 | 34 |  |  |  |  |

TABLE 2

Effect of mid-cycle photic stimulation on 41 menstrual cycle lengths of 16 women aged 16 to 36 years

| Menstrual cycle length (days) | 25 | 26 | 27 | 28 | 29 | 30 | 31 | 32 | 33 | 34 | 35 | 36 | 37 | 38 | 39 | 40 | 41 | 42 | 46 | 49 | Totals |
|---|---|---|---|---|---|---|---|---|---|---|---|---|---|---|---|---|---|---|---|---|---|
| No of control cycles (A) | 2 | 7 | 2 | 2 | 5 | 1 | 6 | 7 | 1 | 3 | 1 | 2 | 1 | 1 | 0 | 0 | 0 | 0 | 0 | 0 | 41 |
| No. of experimental cycles (B) | 2 | 2 | 2 | 5 | 11 | 7 | 6 | 1 | 0 | 1 | 0 | 0 | 1 | 0 | 0 | 0 | 1 | 0 | 1 | 1 | 41 |

We obtained 41 controls and 41 matching experimental cycle lengths, each of the 16 subjects contributing the same number of experimental cycle lengths as controls. The results are presented in Tables 1 and 2 and FIG. 1. A comparison of the two histograms in FIG. 1 shows that the experimental cycle lengths (B) were, on the whole, less variable than the control cycle lengths (A), and that in addition, there was a relatively sharp peak at 29 days in the experimental histogram (B). In contrast, the histogram (A), for the control cycles, appears to spread out with many lower level peaks.

In order to determine whether the spreads of the two histograms differed in a statistically significant manner, we set out to compare the control vs. the experimental values. According to the assumed hypothesis, the spread of the experimental cycle lengths should be significantly reduced as compared to that of the control cycle lengths. The familiar F variance ratio test, which is usually employed to make such comparisons, is not valid in the present case. This is because menstrual cycles do not follow the normal distribution, and in addition, the subjects serve as their own controls and hence the populations of cycles being compared are not independent. We therefore sought a distribution free test, which would not be subjected to these objections. This was provided to us by Prof. I. J. Good of the Virginia Polytechnic Institute and State University. This test depends on the ranges of the cycle lengths for each subject.

TABLE 3

| Subject | 1 | 2 | 3 | 7 | 9 | 16 | 17 | 18 | 22 | 23 | X |
|---|---|---|---|---|---|---|---|---|---|---|---|
| Control range | 11 | 4 | 6 | 1 | 11 | 7 | 3 | 2 | 2 | 5 | 9 |
| Experimental range | 4 | 2 | 3 | 4 | 9 | 2 | 1 | 3 | 1 | 0 | 3 |

Specifically our object is to find out if the ranges of the experimental cycle lengths are, on the whole, shorter than the ranges of the control cycle lengths. Ignoring ties and cases where there is no range (i.e. when there is only one observation), we obtain Table 3. We now calculate the probability that this result, or better, will occur by chance alone. This is given by $$\frac{11!}{2^{11}}\left(\frac{1}{9!2!} + \frac{1}{10!1!} + \frac{1}{11!0!}\right) = 0.0327$$

This probably is identical to that of throwing nine heads out of eleven tosses of a coin. The result of 3.3% level of significance can be regarded as sufficient basis to the claim that a large scale experiment is now fully justified. This datum represents the total experimental evidence to date.

We conclude that the statistical results obtained here are very encouraging. In the eleven subjects exposed to light for more than one cycle, nine showed a decrease in the range of cycle length. In addition, the 29-day peak in the histogram (FIG. 1) is a salient feature.

We attempted to find a temporal relationship between the regularized cycle-length and basal body temperature recorded in most of the experimental cycles, but were unsuccessful. In this connection it is of interest that Morris et al (1976) failed to demonstrate a complete correlation between the temperature nadir and the luteinizing hormone (LH) surge in a group of 27 normal women. Hence they regard the temperature graph as an unreliable method for pinpointing the time of ovulation. They conclude their report by stating "For both fostering conception and preventing pregnancy, BBT is an unsatisfactory signal".

In future experiments it would be desirable to obtain more reliable measurements of ovulation in relation to photic stimulation by, for example, measuring serum LH surges via radioimmunoassay techniques. Certain primates whose ovulation can be detected directly by palpation would also certainly be helpful in such experiments. Future experiments with human subjects would be improved by keeping records of the time of going to bed and turning the light off and the time of getting up in the morning. There is already some published information, which is consistent with the theoretical implication that frequent and large changes in time zones can induce menstrual irregularity.

While the control cycles in our data seem to have the same irregularity independently of whether they were obtained before or after the experimental regimen with light, it should be mentioned that, in the case of subject X, there is a suggestion that after her long regimen with light there was a temporary regularity for the first few control cycles (see Table 4).

In view of our statistical results and other published observations as well as of the recent reports of deleterious side effects of the Pill and from the IUD, it seems worthwhile to continue our tests on a much larger group of women.

If the period of the fertility cycle of a woman could be influenced in some way to become highly regular, then the rhythm method, which has serious drawbacks at present, would become a valuable and reliable technique for birth control. It would be especially valuable for populations that are culturally, economically, or medically prevented from using other methods currently available.

It is very common in biology to find synchronization or "entrainment" phenomena between environmental influences and various types of rhythms, such as EEG, ECG, and circadian rhythms. This "entrainment" or "locking in step" phenomenon can also result in a regularization effect. This is illustrated in FIG. 2, which shows the regularization of an irregular electronic oscillator, by entrainment with a very regular external periodic stimulation. Therefore, it seems useful to consider the possibility of entraining the ovulation cycle. While there are encouraging indications that this might be accomplished by the periodic administration of drugs, one should not overlook the possibility of photic stimulation, since it is well known that photic stimulation can profoundly affect the pituitary-gonadal function in many vertebrates.

In addition, there are a number of references to the effect of moonlight on the breeding of marine animals, many of which date from antiquity. (Aristotle said that the ovaries of sea-urchins were unusually large at the time of full moon and Cicero noted that all shell fish alter in size with the moon.) Cloudsley-Thompson summarized the scientific observations of lunar entrainment of sexual cycles of marine animals in his book. Of especial importance is the work of Hauenschild who demonstrated that such lunar entrainment is accomplished by photic stimulation. He succeeded in entraining the sexual form of the worm, Platynereis dumerilii, by nocturnal photic stimulation for 6 nights every 30 days with a 15-watt bulb (0.02–0.1 lux).

Since the average period of the human and subhuman primate fertility cycle is nearly a lunar period (29.5 days), it is conceivable that it could possibly be entrained in a similar manner by photic stimulation. One way to test this idea was suggested in conversation by N. Wiener: "See if the menstrual cycles of primates are entrained by moonlight at the equator." Considerations of the scheduling and average intensity of the full moon as well as the possibility of continuous outdoor existence would favor such a geographic location. As reported in the book of Ellis, a surgeon in the Dutch Army, named Hill, noted that guenon monkeys in Surinam, South America (within 7 degrees from the equator), exhibited". . . an abundant sanguineous flow occurring at every new moon and lasting about three days, the animal at this time showing signs of sexual excitement." This would imply that ovulation occurs at full moon.

Encouraged and guided by these considerations, we designed the following experiment and initially performed it on one subject. A common bedroom table lamp with a shade which projects light to the walls and ceiling was placed on the floor at the foot of the subject's bed so that all illumination was indirect and minimally disturbing. A 100-watt bulb was used, but in view of Hauenschild's work, much less would probably suffice. The light was kept on the entire nights of the fourteenth, fifteenth, sixteenth, and seventeenth days of the subject's cycle, day 1 being the first day of menstrual flow. If the subject's cycle is irregular, this regimen should make it become regular if entrainment can take place.

Table 1 gives the results of such a regimen on the first subject who was 26 years old and whose reportedly varied previously between 33 and 48 days over a 16 year period. During the first two 29 day cycles she was unaware of the experiment and was informed only to relieve her anxiety aroused by the deviation of her cycle from its previous behavior. The fourth cycle, which lasted 35 days, occurred when the light was turned off a few hours before dawn. This may indicate that it is essential to have a relatively continuous "pulse" of light in order to induce ovulation. If this cycle were omitted from the data (a dangerous procedure in small sample statistics) the probability that the periods with light are from a different statistical population than those without light is $P > 0.995$ according to the F variance ratio test.

Table 5 shows cycles of a different subject undergoing a modified regimen of one night of stimulation. This subject occasionally experienced pain in the middle of her cycle, presumably mittelschmertz, and it is interesting that this pain, much intensified, was experienced on the two occasions after one night of photic stimulation (on the fourteenth night).

Further research with this experiment and some modifications of it are now being undertaken by Rock at his clinic on several patients with irregular cycles. This work will be published jointly when the results become available.

TABLE 4

Effects of photic stimulation on the menstrual cycle of the first subject (aged 26)*

| Cycle | Date of Menstruation | Dates of photic stimulation | Cycle length |
|---|---|---|---|
| 1 | 5/8/65 | 5/23, † 24, 25 | 29 |
| 2 | 6/6/65 | 6/19, 20, 21, 22 | 29 |
| 3 | 7/5/65 | 7/18, 19, 20 | 29 |
| 4 | 8/3/65 | 8/16, 17, 18 | 35‡ |
| 5 | 9/7/65 | 9/20, 21, 22, 23 | 31 |
| 6 | 10/8/65 | 10/21, 22, 23, 24 | 30 |
| 7 | 11/7/65 | 11/20, 21, 22, 23 | 29 |
| 8 | 12/6/65 | No stimulation | 32 |
| 9 | 1/7/66 | No stimulation | 32 |
| 10 | 2/8/66 | No stimulation | 29 |
| 11 | 3/9/66 | No stimulation | 38 |
| 12 | 4/16/66 | No stimulation § | 31 |
| 13 | 3/17/66 | No stimulation | 27 |
| 14 | 6/13/66 | No stimulation | 35 |
| 15 | 7/18/66 | | |

*Photic stimulation from a 100-watt light bulb was supplied during the entire nights of the fourteenth, fifteenth, sixteenth, and seventeenth days of the subject's menstrual cycle. Previously the subject's cycle tended to be long and irregular (reported as 33–48 days). The photic stimulation on cycles 1 and 2 was given without the subject's knowledge. Best estimates of population variance (using Bessel's correction) are 0.7 day$^2$ with light (omitting cycle 4; see text), 13.3 days$^2$ without light. $F^{R/5} = 19$, i.e., $P > 0.995$ that the two series are from different statistical populations. Deviations from the experimental design are as follows: cycles 1, 3, and 4 had only 3 nights of stimulation.
†Day 16 instead of 14 was used.
‡Light was terminated before dawn (see text).
§On these nights (days 7 and 8) a very weak light was accidentally present.

TABLE 5

Evidence of photically induced ovulation in a second subject (aged 38) with mittelschmerz

| Cycle | Date of Menstruation | Dates of photic stimulation | Dates of mittelschmerz | Cycle length |
|---|---|---|---|---|
| 1 | 1/8/67 | No stimulation | | 28 |
| 2 | 2/4/67 | No stimulation | | 33 |
| 3 | 3/8/67 | 3/21, 22† | 3/22/67 | 33 |
| 4 | 4/9/67 | 4/22/67‡ | | 29 |
| 5 | 5/7/67 | 5/21/67§ | | 32 |
| 6 | 6/7/67 | No stimulation | | 33 |
| 7 | 7/3/67 | 7/22/67 | 7/23/67 | 28 |
| 8 | 8/6/67 | | | |

*This subject had a history of mild cramps around the presumed time of ovulation. On the two occasions when a 75-watt light bulb was left on all night of the fourteenth day(placed on a bureau 2 feet from the bed on cycle 3 and on the floor next to the bed on cycle 7) the subject reported an unusually severe mittelschmerz during the following day. In contrast to Table 1, the photic stimulation was confined to one night (except for cycle 3).
†The light was turned off before dawn on the second night.
‡A 40 watt bulb in an open closet 6 to 8 feet from the bed was used.
§The light was turned off at about 4 a.m.

The possible mechanism for photically induced ovulation would undoubtedly involve the hypothalamus-pituitary system as well as possibly the pineal gland. The latter is suggested by recent researchers on the pineal gland of mammals which seems to indicate that melatonin is controlled by the enzyme hydroxyindole O-methyl transferase can play an important role in photically induced genital effects. It may well be that light induces through such mechanisms a sudden pulse of LH since it is known that a sudden increase in LH in the presence of ripe follicles can induce ovulation. Our point in mentioning these things at this time is to indicate that possible mechanisms exist for the effect we are investigating.

In conclusion, it appears that it would certainly be worthwhile to investigate further the possibility of entraining the ovulation cycle of human females by photic stimulation. If a high degree of regularization were to occur for a significant percent of the population, then the rhythm method, with its various advantages for some people, could be used more effectively.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A luminescent ovulation/menstrual cycle adjustment process to entrain preselected biorhythms with a scheduled regimen of photic stimulation, said process comprising the steps of:

subjecting a woman subject to a nocturnal light exposure that corresponds exactly to a lunar schedule of brightness in both period and intensity with a maximum nocturnal brightness corresponding with a full moon, and diminishing to zero brightness at the new moon; and repeating the subjecting step with regular periodicity.

2. A luminescent ovulation/menstrual cycle adjustment process to entrain preselected biorhythms with a scheduled regimen of photic stimulation, as defined in claim 1, wherein the subjecting step is accomplished using a light source with a variable amplitude of brightness such that said nocturnal light exposure has a ½ sinusoidal amplitude with a period of 29.5 days of brightness with a maximum nocturnal brightness corresponding with a full moon.

3. A luminescent ovulation/menstrual cycle adjustment process to entrain preselected biorhythms with a scheduled regimen of photic stimulation, as defined in claim 1, wherein the subjecting step is accomplished using a red light source with a variable amplitude of brightness such that said nocturnal light exposure has a ½ sinusoidal amplitude with a period of 29.5 days of brightness with a maximum nocturnal brightness corresponding with a full moon.

\* \* \* \* \*